United States Patent [19]

Dearling

[11] 4,341,348

[45] Jul. 27, 1982

[54] DIRECT AND INDIRECT FRAGRANCE DISPENSING DEVICE

[76] Inventor: Neal S. Dearling, 132 E. 35th St., New York, N.Y. 10016

[21] Appl. No.: 205,430

[22] Filed: Nov. 10, 1980

[51] Int. Cl.³ .............................................. A61L 9/04
[52] U.S. Cl. ...................................... 239/34; 239/326
[58] Field of Search ....................... 239/34, 44, 47, 49, 239/50, 51.5, 53, 55, 57–60, 289, 326; 222/182, 187, 402.17

[56] References Cited

U.S. PATENT DOCUMENTS

| 3,101,905 | 8/1963 | Hoenig | 239/326 X |
| 3,330,481 | 7/1967 | Dearling | 239/47 |
| 3,940,024 | 2/1976 | Russo et al. | 222/402.17 X |
| 3,972,473 | 8/1976 | Harrison | 239/34 |
| 4,084,732 | 4/1978 | Dearling | 239/34 X |

Primary Examiner—Johnny D. Chery
Attorney, Agent, or Firm—Curtis, Morris & Safford

[57] ABSTRACT

A fragrance dispensing device to provide a fragrance or scent by direct or indirect means comprising a container to discharge a quantity of a suitable fragrance, such as a perfume or deodorizer, and a cover assembly for the container to permit direct discharge in the form of a spray of the fragrance or scent and also to confine the spray discharge within the cover assembly where it is absorbed or adsorbed on a carrier member so that the fragrance or scent may be dissipated over a longer period of time.

5 Claims, 5 Drawing Figures

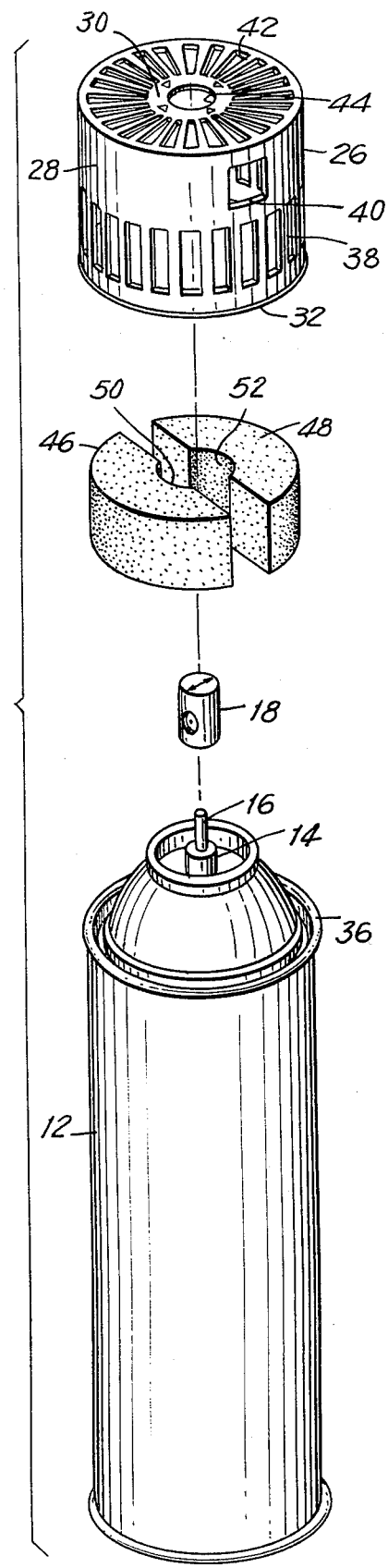
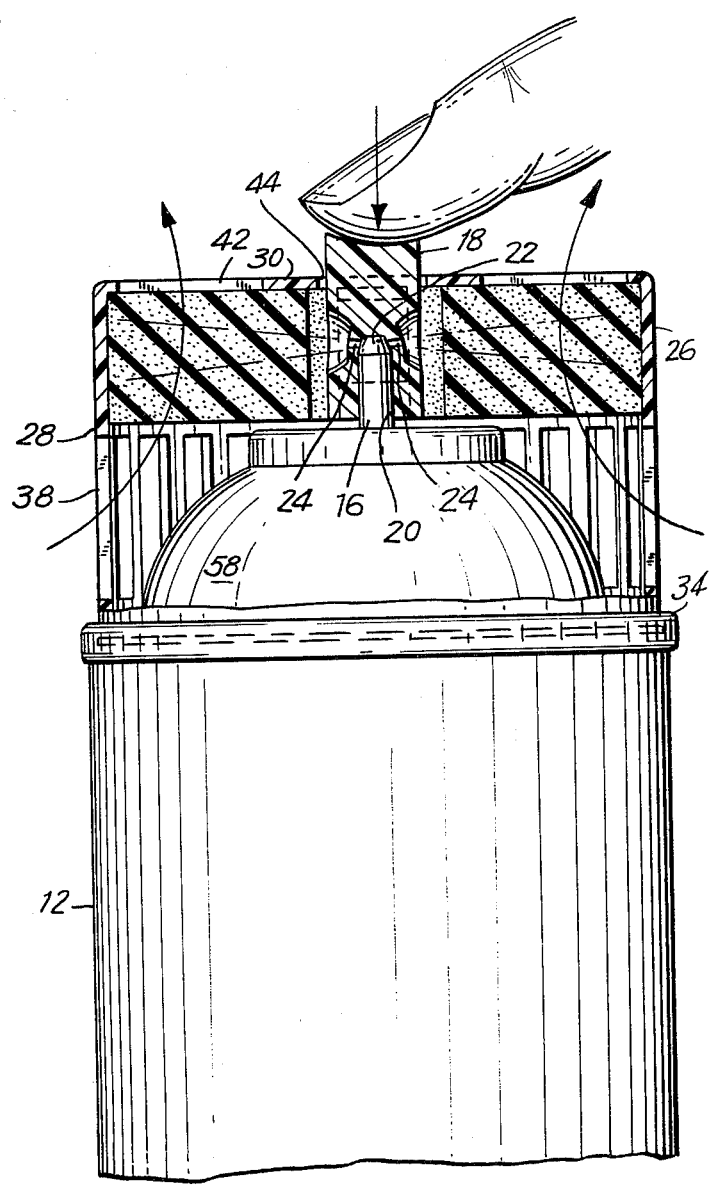

DIRECT AND INDIRECT FRAGRANCE DISPENSING DEVICE

The present invention relates to a scent or fragrance dispensing device, and more particularly to a scent or fragrance dispensing device that dispenses a measured quantity of a spray fragrance as a vapor spray directly into the air and which may also dispense a fragrance or scent indirectly into an absorbent or adsorbent carrier member so that the fragrance or scent is dissipated over a longer period of time.

Broadly, the present invention comprises a container adapted to discharge a quantity of a suitable scent or fragrance, such as a perfume or a deodorizer, by either directly discharging a spray mist on diametrically opposed sides directly into the air and by discharging a quantity of the fragrance or spray into diametrically opposed carrier members capable of absorbing or adsorbing the liquid fragrance or scent and to dissipate the aroma over a long period of time. The device utilizes a container to hold the liquid fragrance or scent and the container may be either an aerosol container, wherein the contents are under pressure and are released through a valve as a spray, or the container may include a suitable pump member which when depressed discharges a quantity of the liquid fragrance or scent as a spray. In one embodiment of the present invention, a cover assembly for the container is provided which has two effective positions for dispensing the fragrance or scent. In a first position the spray is released from the container through diametrically opposed openings on either side of the container so as to spray directly into the air from diametrically opposed sides. In a second position, the diametrically opposed sprays impinge upon suitable carrier members which are disposed within the cover assembly and which absorb or adsorb the fragrance and then slowly dissipate the aroma over a prolonged period of time.

Devices of the type disclosed herein have a number of uses, including particularly to provide an effective room deodorizer where the device can be set to spray an appropriate deodorizing spray directly into the room to dissipate offensive odors. The device may also be used to cause the spray to impinge upon the carrier members which absorb or adsorb the deodorizing agent to slowly dissipate a pleasant aroma over a longer period of time to maintain the pleasant aroma in the room. Another use for devices of the present type is for dispensing pharmaceutical preparations, for example decongestants and the like, into a room and then to spray the decongestant onto the carrier members to maintain the beneficial aroma in the room for a longer period of time.

In order to make an effective device of this type it is imperative to provide a means to sufficiently wet the absorbent or adsorbent carrier member so that enough of the fragrance or scent is retained by the carrier members to provide a prolonged period of time in which the fragrance or scent may be dissipated. Concurrently with providing a means to increase the quantity of the liquid fragrance or scent retained by the carrier members it is also necessary to provide an effective path for air flow through and around the carrier members so that the retained liquid fragrance or scent can be effectively dissipated.

Devices have been proposed heretofore which may used for the same purpose as the invention herein. Such devices are disclosed and described in U.S. Pat. Nos. 3,330,481, 3,940,024, 3,972,473 and 4,084,732. However, none of the devices shown in these prior patents provide a device capable of retaining a greater quantity of the liquid fragrance or scent in a carrier member coupled with the ability to provide an increased and more effective air flow in and around the carrier member for increased effectiveness in dissipating the aroma or scent over a long period of time.

In the device disclosed in U.S. Pat. No. 3,330,401, no provision is made for both direct and indirect spraying of the scent or fragrance and, while this device has been generally effective to dissipate a scent or fragrance over an extended period of time, the present invention is more effective in that respect because of the increased capacity of the carrier member to retain a greater quantity of the scent or fragrance.

In the device shown in U.S. Pat. No. 3,940,024, a complex cap structure is required which is difficult to use and which fails to provide an effective manner of absorbing or adsorbing large quantity of liquid scent or fragrance. In addition the air flow pattern used with that device is not as effective as the air flow pattern embodied in the present invention.

In the device shown in U.S. Pat. No. 3,972,473, the absorbent material is of limited area and the device fails to provide an effective air flow pattern to maximize the dissipation of the fragrance or scent over a long period of time.

The device shown in U.S. Pat. No. 4,084,732, while showing an improved structure over the three prior patents, shows a device which requires an effective transfer of the liquid fragrance or scent from an initial carrier member to another carrier member by a wicking action which limits the quantity of the fragrance or scent which can be absorbed or adsorbed by the carrier member.

Accordingly, it is an object of the present invention to provide a fragrance or deodorizer dispensing device wherein the fragrance or deodorizing agent may be dispensed either as a spray directly into the air or dissipated over a longer period of time in a more effective manner than heretofore provided.

It is a further object of the present invention to provide such a direct and indirect fragrance dispensing device by providing a cover assembly for a container or fragrance which in one position permits direct spray of the fragrance into the air and in another position permits the absorption or adsorption of a quantity of the fragrance onto a carrier member for slower dissipation of the fragrance.

These and other objects and advantages of the present invention will become more readily apparent after consideration of the following specification and accompanying drawing wherein:

FIG. 2 is an exploded perspective view showing a preferred embodiment of the present invention;

FIG. 3 is a sectional view taken on line 3—3 of FIG. 1 showing the device of the present invention positioned for dispensing the fragrance or scent directly into a carrier member;

Figure 1:
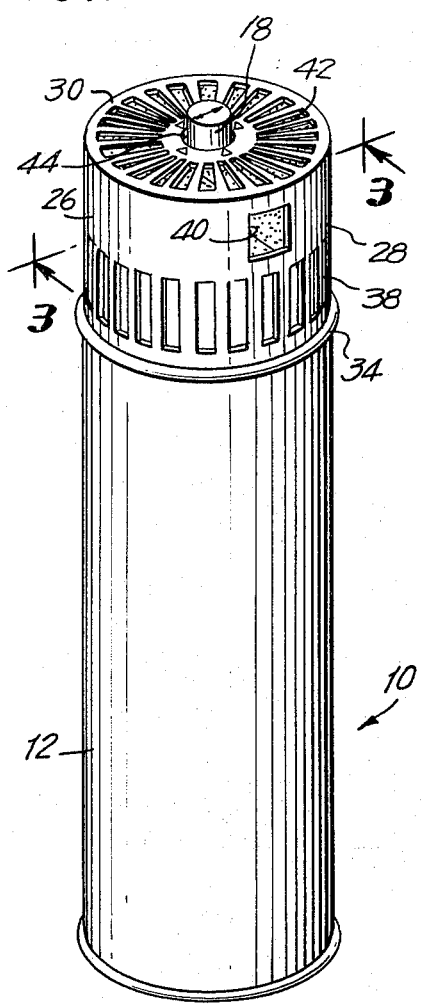
FIG. 1 is an overall perspective view showing a preferred embodiment of the direct and indirect fragrance dispensing device of the present invention.

With reference to the drawing and particularly FIGS. 1 and 2, the direct and indirect fragrance or scent dispensing device 10 of the present invention includes a container 12 to hold a quantity of an appropriate fragrance, scent or deodorizer. Container 12 includes a closure assembly 14 within which is housed a suitable valve (not shown) terminating in a valve actuation stem 16. Valve stem 16 is typically spring loaded and upon downward depressing of valve stem 16 the valve opens permitting the liquid scent or fragrance within container 12 to be ejected under pressure through valve stem 16. However, it is to be understood that when the container 12 is of the non-aerosol type, valve stem 16 would be a pump actuator stem which upon repeated depression would permit the exiting of liquid from container 12.

A plunger element 18 is also provided (see FIGS. 3 and 4 as well) to be frictionally engaged over the valve stem 16. Plunger element 18 includes a cylindrical bore 20 adapted to frictionally engage valve stem 16 with bore 20 terminating in a frusto-conical shaped chamber 22 which communicates with diametrically opposed radiating access ports 24 through which the spray of liquid under pressure emanates when valve stem 16 is depressed.

A cover member 26 is provided comprising a substantially cylindrical wall portion 28, an end wall 30 and an opposite open end 32. The end of cylindrical wall 28 near the open end 32 is outwardly flanged as at 34 so that the cover assembly 26 can frictionally engage around the rolled lip 36 of the container 12 so that the cover assembly is securely frictionally engaged on the container 12.

Figure 4:
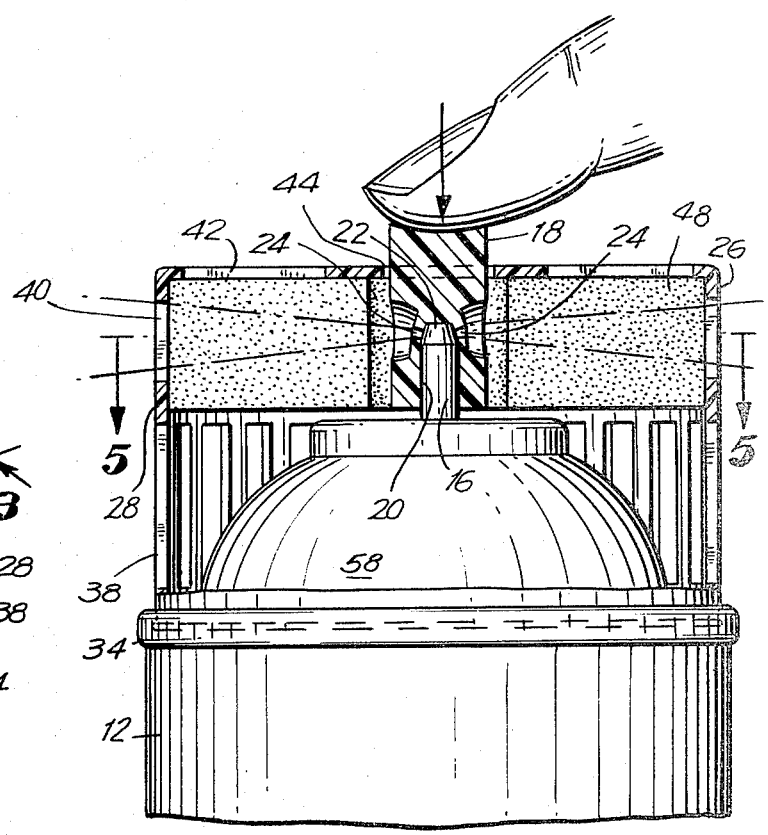
FIG. 4 is a view similar to FIG. 3 showing the device of the present invention positioned for dispensing the fragrance or scent into the room.

A plurality of circumferentially spaced rectangular slots or openings 38 are provided in wall 28 of cover 26 in the lower portion of wall 28 adjacent the flanged portion 34. These openings or slots 38 are spaced uniformly about the circumference of wall 28 and permit free flow of air into and out of the cover 26 when it is placed in juxtaposition over a container 12. Wall 28 also includes diametrically opposed spray access openings 40 therein on each side of the cover. Openings 40 are aligned with spray ports 24 in one position, as seen in FIG. 4, so that when valve actuator 16 is appropriately depressed, the spray of the fragrance or scent emanating from container 12 can pass directly out access ports 40 into the atmosphere. Wall 30 of cover 26 also includes a plurality of circumferentially spaced radiating slots or access ports 42 and a central aperture 44 through which plunger element 18 extends.

Figure 5:
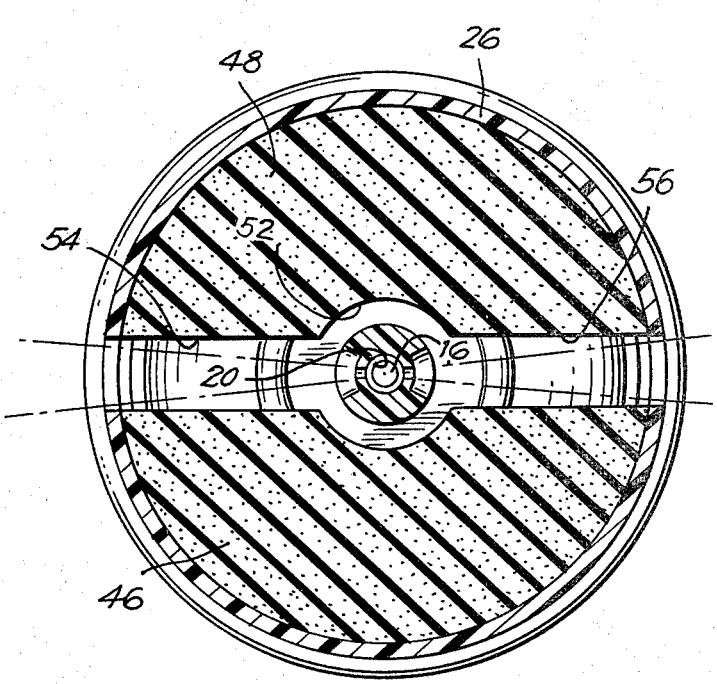
FIG. 5 is a sectional view taken along line 5—5 of FIG. 4.

Within cover 26 a pair of carrier members 46 and 48, respectively, are placed. Carrier members 46 and 48 are each substantially semicircular in cross section and are preferably of an absorbent or adsorbent material, for example, spongy-like material having the ability to soak up and retain the liquid fragrance or scent and to dissipate the aroma from the fragrance or scent as the liquid slowly evaporates over a long period of time. Carrier members 46 and 48 are disposed within cover 26 adjacent the wall 30 and within the cover 26 above the location of the access slots 38. Each includes a semicircular cutout portion 50 and 52, respectively, which is spaced radially outwardly from the outer circumference of valve plunger member 18 and when placed in cover 26 (see FIG. 5) are spaced from each other to provide diametrically opposite passages 54 and 56 so that when the spray ports 24 are aligned with passages 54 and 56, the spray emanating therefrom will pass freely out of the access ports 40 for spraying directly into the atmosphere. When either cover 26 or the valve plunger member 18 is rotated 90° from the position shown in FIG. 5, actuation of the spray valve will direct the spray from spray ports 24 directly into the absorbent or adsorbent carrier members 46 and 48 where the scent or fragrance is retained for slow evaporation and dissipation of the aroma. Carrier members 46 and 48 may be secured in cap 26 in any convenient manner, for example, bonding by glue or by frictional fit.

As is best evident in FIG. 3, with the arrangement of the carrier members 46 and 48 above the access passages 38 an air flow path is provided in either direction through access passages 38, then through the carrier member of spongy-like material and out access passages 42. With this arrangement which is enhanced by the generally dome-shaped segment 58 of the top of container 12, a positively directed flow path for ambient air is maintained which efficiently allows free passage of the air through the carrier member to greatly increase the efficiency of the aromatic dissipation.

It is thus seen that the present invention provides a simple yet effective structure permitting both the direct spraying of a scent or fragrance into a room and the slow dissipation of the aroma over a longer period of time. By use of a pair of diametrically opposed carrier members, a greater quantity of a scented liquid can be directly absorbed or adsorbed as the scented liquid is directed into each carrier member by the diametrically opposed spray ports. The cap member is designed to maximize the effectiveness of ambient air flow through and around the moistened carrier members to dissipate the aroma over a long period of time more effectively than the prior art devices shown in the above mentioned patents.

It is also apparent that, if desired, additonal spray parts may be provided in plunger element 18 so that upon actuation of plunger 18 the spray may simultaneously wet carrier members 46 and 48 and spray directly out of the spray access openings 40.

What is claimed is:

1. A fragrance dispensing device for direct or indirect dissemination of a fragrance comprising:
    a cover member adapted to be positioned over the discharge outlet means of a fragrance container,
    said cover member including means to provide an access passage from within said cover member to the exterior of said cover member on diametrically opposed sides of said cover member,
    a pair of carrier members having the ability to absorb or adsorb a liquid fragrance disposed within said cover member on diametrically opposite sides of said cover member,
    actuation means including a fragrance spray outlet member having at least a pair of spray outlet ports therein on diametrically opposed sides thereof and cooperable with said discharge outlet means to discharge a spray of said fragrance from said outlet ports,
    said actuation means and cover member being movable relative to each other between a first position wherein said outlet ports are oriented in register with said access passages in said cover member to discharge said fragrance directly to the exterior of said cover member as a spray and a second position wherein said outlet ports are oriented to discharge said fragrance onto said carrier members within said cover assembly to disseminate said fragrance indirectly over a long period of time, and means within said cover member to direct a flow of air into and around said carrier members.

2. A fragrance dispensing device as defined in claim 1 wherein said cover member comprises a cylindrical wall member, an end wall member and an open end and wherein said means to direct a flow of air includes a plurality of access openings circumferentially spaced about said cylindrical wall member and in said end wall member thereby to provide an air flow path into and through said cover member when it is positioned on said fragrance container.

3. A fragrance dispensing device as defined in claim 2 wherein said carrier members are disposed within said cover member spaced from each other to provide a spray access passage from said outlet ports to the exterior of said cover member when said actuation means and cover member are in said first position and are positioned in the path of a spray emanating from said spray outlet ports when said actuation means and cover member are in said second position.

4. A fragrance dispensing device as defined in claim 3 wherein said carrier members are disposed above said circumferentially spaced access openings in said cylindrical wall member and in juxtaposition to said access openings in said end wall member wherein said air flow path is directed through said cover member and through said carrier members.

5. A fragrance dispensing device as defined in claim 1 wherein said cover member includes an access opening in said end wall member adapted to receive an end of said fragrance spray outlet member therethrough such that said fragrance spray outlet member is accessible from the exterior of said cover member.

* * * * *